United States Patent [19]

Schoenwald et al.

[11] Patent Number: 4,975,447
[45] Date of Patent: Dec. 4, 1990

[54] 6-HYDROXYETHOXY-2-BENZO-THIAZOLESULFONAMIDE AND TOPICAL TREATMENT COMPOSITIONS AND METHOD FOR GLAUCOMA

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 720,007

[22] Filed: Apr. 4, 1985

Related U.S. Application Data

[63] Continuation-in-part of Ser. No. 464,063, Feb. 13, 1983.

[51] Int. Cl.$^5$ .................. A61K 31/425; C07D 277/62; C07D 277/68; C07D 277/76
[52] U.S. Cl. .................................... 514/367; 514/913; 548/166
[58] Field of Search ................ 514/367; 548/164, 167, 548/166

[56] References Cited

U.S. PATENT DOCUMENTS 4,505,923  3/1985  Hoffman, Jr. et al. ............. 514/367

OTHER PUBLICATIONS

Chem. Abst. 102:137644(g) (1985)–Lewis et al.
Chem. Abst. 102:197524(c) (1985)–Eller et al.

Primary Examiner—Douglas W. Robinson
Attorney, Agent, or Firm—Zarley McKee, Tromte, Voorhees & Sease

[57] ABSTRACT

A topical composition for eye treatment of glaucoma, comprising a small but pharmaceutically effective amount of an analog of benzothiazole-2-sulfonamide. The most preferred compound is 6-hydroxyethoxy-2-benzothiazolesulfonamide. The invention also relates to a method of topically treating glaucoma with eye drops to reduce intraocular pressure. Finally, disclosed is a method of synthesis of the preferred and highly effective benzothiazole-2-sulfonamide analogs, particularly the 6-hydroxyethoxy-2-benzothiazolesulfonamide compound.

14 Claims, No Drawings

6-HYDROXYETHOXY-2-BENZOTHIAZOLESULFONAMIDE AND TOPICAL TREATMENT COMPOSITIONS AND METHOD FOR GLAUCOMA

GRANT REFERENCE

This invention was made in part with government support under Contract No. 5 RO1 EY No. 03297-02 awarded by the National Eye Institute. The government may have certain rights in this invention.

CROSS REFERENCE TO A RELATED INVENTION

This application is a continuation-in-part of copending, commonly assigned application Ser. No. 464,063, filed Feb. 13, 1983.

BACKGROUND OF THE INVENTION

Glaucoma, which some estimate affects 2 million adults over 40, is an impairment of vision caused by too much fluid pressure within the eye.

Surgical treatment for glaucoma is effective, however, it is expensive and some surgeons will use surgery only as a last resort.

Carbonic anhydrase inhibitors, prescribed orally work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness, comes nausea, tingling in fingers and toes and other side effects. Oral drugs generally do not, however, cause side effects in the eye.

Certain topical drugs, while causing less systemic effects, on the other hand, can cause sever headaches and constrict the pupil, making the daytime appear dark.

Accordingly, there is a real and continuing need to develop an inhibitor drug that can be dropped into the eye instead of swallowed, thereby avoiding the present side effects. It is a primary objective of the present invention to develop a highly effective topical carbonic anhydrase inhibitor drug for treatment of glaucoma to reduce intraocular eye pressure, and at the same time, avoid the systemic side effects, commonly caused by oral drugs.

Another objective of the present invention is to develop a drug for topical treatment of glaucoma, which is not only effective, but which will also pass through the three layered cornea and still be effective enough to work on the ciliary body.

Another objective of the present invention is to develop a highly effective, topical drug treatment for glaucoma which is substantially non-harmful to the eye when topically applied.

An even further objective of the present invention is to develop an eye treating topical composition which is effective for glaucoma treatment.

A still further objective is to provide a convenient method of synthesis of 6-hydroxyethoxy-2-benzothiazolesulfonamide, which is a highly effective topical treatment of glaucoma.

A further specific objective of the present invention is to provide as a novel component 6-hydroxyethoxy-2-benzothiazolesulfonamide, in pharmaceutically effective amounts is a highly effective topical composition for eye drop treatment of glaucoma.

The method and manner of achieving each of the above objectives, as well as others, will become apparent from the detailed description of the invention which follows hereinafter.

SUMMARY OF THE INVENTION

As a new compound, 6-hydroxyethoxy-2-benzothiazolesulfonamide. Also, topical compositions for eye drop treatment of glaucoma which comprises a small but pharmaceutically effective amount of 6-hydroxyethoxy-2-benzothiazolesulfonamide.

The invention thus relates to a most preferred compound which is a compound falling into the general formula presented in our previous patent application, Ser. No. 464,563, filed Feb. 13, 1983. The invention further relates to a method of topically treating glaucoma with eye drops to reduce intraocular eye pressure; and finally, the invention relates to a method of synthesis of this preferred compound.

DETAILED DESCRIPTION OF THE INVENTION

As heretofore mentioned, carbonic anhydrase inhibitors are known. However, the compounds are generally not effective because of the rather severe side effects previously mentioned. Studies have shown that when taken orally, because of the side effects, approximately 80% of the treated patients stop taking the drug treatment within two to three weeks. The side effects that they often report are short-term tingling of the extremities, gastrointestinal tract upset, kidney stones and some renal failure.

The mechanism of reaction of carbonic anhydrase inhibitors has been reported, and it is a combination of a diuretic effect and reduction of intraocular pressure in the eye. The compound useful for treatment in this invention functions to provide reduction of intraocular pressure, but does so without the commonly occurring side effects of oral drugs for treating glaucoma, or the commonly occurring side effects of topical drugs for glaucoma treatment.

The compound developed by the applicant and useful for the topical composition eye drop treatment of glaucoma, as described in this invention, is an analog of benzothiazole-2-sulfonamide, and is a carbonic anhydrase inhibitor. It has the following general formula:

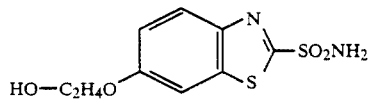

It is also to be understood that one may use an ophthalmologically acceptable salt of the above shown compound. Examples of acceptable salts include the alkali metal salts.

Of course, the compound is carried in an inert, noneye irritating, non-toxic eye drop diluent of conventional formulation. Such formulations are well known, and commonly referred to in, for example, the *Physician's Desk Reference for Ophthalmology* (1982 Edition, published by Medical Economics Company, Inc., Oridell, New Jersey), wherein numerous sterile ophthalmologic ocular solutions are reported, e.g., see pp. 112–114, which are incorporated by reference.

Preferably the amount of 6-hydroxyethoxy-2-benzothiazolesulfonamide present in the eye drop treatment composition is a concentration of from about 0.25% to about 5% by weight of the eye drop treating composition. Most preferably, the amount is from about 0.5% to about 3.0% by weight of the eye drop treating composition, and in tests conducted to date, highly effective compositions have used the compounds at the 1% and 3% suspension level.

As heretofore mentioned, while the diluent is not part of the present invention in that such diluents are known, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 6.8 to about 7.8.

Commonly used wetting agents are well known, and again are mentioned in the previously referred to pages of the *Physician's Desk Reference for Ophthalmology*. One suitable one is Tween, and in particular, Tween 80. Likewise, antibacterials are known and commonly employed in such compositions. Suitable anti-bacterials include the most preferred benzalkonium chloride and others as well such as, for example, chlorobutanol. The amount of wetting agent can range from .01% to .10%.

The amount of anti-bacterial can range from about 0.004% to about .02% by weight of the eye drop treating composition.

The compounds of this invention, providing that the molecular structures are as defined hereinbefore, are water soluable, but they also have a lipid solubility factor to allow transfer across the eye, and they have suitable structure to allow them to effectively function in the eye as carbonic anhydrase inhibitors. Their water solubility means ease of preparation for topical application, their lipid solubility characteristics mean effectiveness in transfer across the three corneal layer.

As will be explained hereinafter, the dosage amounts can vary, and no doubt will vary, but are well within routine experimentation of the treating physician. In some of the tests described hereinafter, the dosage for the topical application has been three drops, with one drop every two minutes. This has been found to be effective, but it is also reasonable to expect that other dosage levels will vary depending upon severity of the case.

The following examples are offered to further illustrate the synthesis of the compounds of this invention, the making of topical treatment compositions using the same, and to provide data showing decrease of intraocular pressure in the eyes of rabbits and cynomolgous monkeys. They are intended to further illustrate, but not necessarily limit the invention and it is understood that certain modifications and changes, both in technique and composition and structure, may be made, without departing from structure, function and operation of the invention.

EXAMPLES

EXAMPLE 1

Synthesis of 6-hydroxyethoxy-2-benzothiazolesulfonamide

The ammonium dithiocarbamate of 4-hydroxyethoxyaniline was prepared by mixing 95% ethanol (50ml) and concentrated ammonium hydroxide (17 ml) in a 3-necked flask equipped with an addition funnel and a thermometer, cooling the solution to $-5°$ C. in an ice-methanol bath, and adding carbon disulfide (10 ml). A solution of 4-hydroxyethoxyaniline (15.7 g, 0.103 mol) in 95% ethanol (50 ml) was added over 30 minutes to the reaction mixture while maintaining a temperature of $0°$ C. The reaction was stirred for 3 hours at $0°$ C. and the precipitated product collected by vacuum filtration in a Buchner funnel. The product was washed with 95% ethanol (50 ml) followed by acetone (25 ml) and air dried at room temperature to give 15.3 g (60.5% yield) of ammonium 4-hydroxyethoxyphenyl dithiocarbamate: m. p. $94°–97°$ C. Ammonium 4-hydroxyethoxyphenyl dithiocarbamate (4.9 g, 0.02 mol) and sulfur (9.7 g, 0.022 mol) were triturated. The reaction mixture was combined in a 25 ml high pressure bomb and placed in a preheated oil bath at $190°$ C. A temperature of $190°–200°$ C. was maintained for a 2 hour period. The bomb was removed from the heating bath and cooled to room temperature. The gases generated by the reaction were passed through as aqueous 5.25% sodium hypochlorite solution. The orange oil was dissolved in aqueous 5% potassium hydroxide (100 ml) and diluted with water (50 ml). The product was precipitated by cooling to $0°$ C. and the pH adjusted to 5 with glacial acetic acid. The precipitated product was collected by vacuum filtration in a Buchner funnel give 1.5 g (33.0% yield) of 6-hydroxyethoxy-2-mercaptobenzothiazole. m. p. $162–165°$ C.; Anal. ($C_9H_9NO_2S_2$) CHN. The sulfenamide was formed by reaction with aqueous sodium hydroxide and sodium hypochlorite and oxidized with m-chloroperoxybenzoic acid to yield the product in 55% yield. m. p. $155°–158°$ C.; Anal. ($C_9H_{10}N_2O_2S_2$) CHN.

EXAMPLE 2

Measurement of Intraocular Pressure ("Salted Rabbit Test") (IOP)

Rabbits (3–4 months old) were maintained on 0.3% sodium chloride solution in place of drinking water for 3 weeks prior to the determination of IOP because it has been shown that a diet deficient in sodium produces a variable response to this class of drugs. During this 3 week period numerous IOP measurements were made to familiarize the rabbits with this procedure. Baseline IOP measurements were determined by applanation tonometry following topical administration of 3 drops of 1% suspension of analog CAI inhibitor to one eye. The fellow eye received blank vehicle. The observer was masked. Each eye received 1 to 2 drops of proparacaine hydrochloride (0.5%) to anethetize the cornea prior to placing the sensor tip of the tonometer flot on the cornea. IOP measurements were determined over 180 minutes at 20 minute intervals. Changes in IOP were expressed as:

IOP change=IOP (dosed eye - control eye)$_t$-IOP (dosed eye prior to administration - control eye)$_{t=O}$ Intraocular pressure (IOP) measurements of 6-hydroxyethoxy-2-benzothiazole sulfonamide in rabbits[a] maintained on 3% sodium chloride drinking water following topical instillation.[b,c]

[a]N=12 rabbits
[b]The dose was 50 μl of a 1% suspension q 2 minutes for a total of 3 doses
[c]Also see: R.A. Lewis, R.D. Schoenwald, M.G. Eller, C.F. Barfknecht and C.D. Phelps, "Ethoxzolamide Analog Gel: A Topical Carbonic Anhydrase Inhibitor," Arch. Ophthalmol., 102, 1821 (1984)

| Time after dosing (minutes) | Ave. change in IOP (mm Hg) | Probability[d] |
|---|---|---|
| 0 | 0 | — |
| 20 | −0.2 | N.S. |
| 40 | −1.1 | 0.07 |
| 60 | −1.1 | 0.04 |
| 80 | −0.8 | 0.12 |
| 100 | −1.2 | 0.04 |
| 120 | −0.5 | N.S. |
| 140 | 0.2 | N.S. |
| 160 | 0.3 | N.S. |
| 180 | −0.2 | N.S. |

[d]N.S. = non-significant, reported values represent probability that the reduction in IOP is due to chance, from student's t test

EXAMPLE 3

As demonstrated in the earlier examples, the compound of the present invention has been demonstrated to inhibit carbonic anhydrase, using the rabbit as the test species. Because there are certain differences in the eyes of rabbits and man, it was desired to test topical carbonic anhydrase inhibition by the compound of the present invention in a subhuman primate species to confirm the presence of activity by this route. The cynomologous monkey was chosen to represent the species. Because drug effects on intraocular pressure are sometimes less dramatic or not demonstrable using an eye that is normotensive, a test protocol known as the "DeSantis" test was developed. It involves testing the carbonic anhydrase inhibitor effects in eyes made hypertensive by laser treatment. In particular, argon laser energy was delivered to the trabecular meshwork of cynomologous monkeys which resulted in an elevation of the intraocular pressure as measured by pneumatonometry. After the eye was allowed to recover from the inflammatory process which accompanied the laser treatment, it was used to test the subject drugs. Experimental results of these tests are reported below.

Intraocular pressure (IOP) was determined using an Alcon Pneumatonograph after light corneal anesthesia with proparacaine, before and at 1, 3 and 7 hours after installation of drug to both eyes of each of six cynomologous monkeys per group. The right eyes of these monkeys had been given laser trabeculoplasty several months prior to this experiment which resulted in ocular hypertension. Animals were trained to sit in restraint chairs and to accept the pressure measurement. Following the measurement, residual anesthetic was washed out with saline.

Data for the intraocular pressure studies are presented in the attached tables, where the lasered eyes but not the normal eyes show significant reduction of intraocular pressure compared to control animals.

In the tables below "OD" refers to ocular dexter, and "OS" refers to ocular sinnister. This is simply another way of saying right and left eye. The designation number in the lefthand column of each table refers to the designation number assigned to each monkey. "SE" refers to standard error. Table 1 shows in the first instance a control treatment of the lasered eye with a gel without the active compound of the invention. In the second instance it shows the treatment of the same eye with the drug, that is with 6-hydroxyethoxy-2-benzothiazolesulfonamide. In the third instance it shows a left eye control and in the fourth instance treatment of the left eye with the drug.

TABLE 1

| | | | 1.0% 6-Hydroxyethoxy-2-benzothiazolesulfonamide Gel | | | | |
|---|---|---|---|---|---|---|---|
| | | | IOP (mmHg) | | | | |
| MONKEY # | EYE | TREATMENT | TIME (HR) | IOP | TIME (HR) | IOP | TIME (HR) | IOP |
| 53 | OD | CONTROL | 0 | 48 | 3 | 48 | 7 | 53 |
| 48 | OD | CONTROL | 0 | 57 | 3 | 57 | 7 | 58 |
| 49 | OD | CONTROL | 0 | 29 | 3 | 28 | 7 | 28 |
| 51 | OD | CONTROL | 0 | 48 | 3 | 40 | 7 | 47 |
| 50 | OD | CONTROL | 0 | 38 | 3 | 31 | 7 | 35 |
| 186 | OD | CONTROL | 0 | 38 | 3 | 35 | 7 | 36 |
| MEAN | | | | 43.0 | | 39.8 | | 42.8 |
| S.E. | | | | 4.0 | | 4.5 | | 4.8 |
| MEAN % CHANGE | | | | | | −7.8 | | −1.1 |
| S.E. | | | | | | 3.3 | | 2.7 |
| 56 | OD | DRUG | 0 | 38 | 3 | 34 | 7 | 34 |
| 47 | OD | DRUG | 0 | 25 | 3 | 23 | 7 | 25 |
| 55 | OD | DRUG | 0 | 28 | 3 | 23 | 7 | 24 |
| 63 | OD | DRUG | 0 | 46 | 3 | 36 | 7 | 46 |
| 52 | OD | DRUG | 0 | 35 | 3 | 30 | 7 | 33 |
| 187 | OD | DRUG | 0 | 48 | 3 | 40 | 7 | 41 |
| MEAN | | | | 36.7 | | 31.0 | | 33.8 |
| S.E. | | | | 3.8 | | 2.9 | | 3.5 |
| MEAN % CHANGE | | | | | | −14.9 | | −7.5 |
| S.E. | | | | | | 2.0 | | 2.7 |
| 53 | OS | CONTROL | 0 | 32 | 3 | 27 | 7 | 31 |
| 48 | OS | CONTROL | 0 | 22 | 3 | 25 | 7 | 24 |

TABLE 1-continued

| | | | 1.0% 6-Hydroxyethoxy-2-benzothiazolesulfonamide Gel | | | | | |
|---|---|---|---|---|---|---|---|---|
| | | | | IOP (mmHg) | | | | |
| MONKEY # | EYE | TREATMENT | TIME (HR) | IOP | TIME (HR) | IOP | TIME (HR) | IOP |
| 49 | OS | CONTROL | 0 | 25 | 3 | 27 | 7 | 28 |
| 51 | OS | CONTROL | 0 | 27 | 3 | 34 | 7 | 32 |
| 50 | OS | CONTROL | 0 | 28 | 3 | 26 | 7 | 28 |
| 186 | OS | CONTROL | 0 | 27 | 3 | 27 | 7 | 31 |
| MEAN | | | | 26.8 | | 27.7 | | 29.0 |
| S.E. | | | | 1.4 | | 1.3 | | 1.2 |
| MEAN % CHANGE | | | | | | +4.1 | | +8.6 |
| S.E. | | | | | | 6.1 | | 3.5 |
| 56 | OS | DRUG | 0 | 33 | 3 | 34 | 7 | 34 |
| 47 | OS | DRUG | 0 | 19 | 3 | 20 | 7 | 25 |
| 55 | OS | DRUG | 0 | 24 | 3 | 25 | 7 | 28 |
| 63 | OS | DRUG | 0 | 23 | 3 | 25 | 7 | 22 |
| 52 | OS | DRUG | 0 | 20 | 3 | 19 | 7 | 19 |
| 187 | OS | DRUG | 0 | 33 | 3 | 38 | 7 | 41 |
| MEAN | | | | 25.3 | | 26.8 | | 28.2 |
| S.E. | | | | 2.5 | | 3.1 | | 3.3 |
| MEAN % CHANGE | | | | | | +5.2 | | +11.1 |
| S.E. | | | | | | 2.7 | | 6.3 |

\*\*NOTE:
Percent change values are calculated from individual animal data and may not reflect changes of mean IOP.

A repeat in order to test the accuracy of the data for the same monkeys was conducted six days later and is reported in Table 2.

TABLE 2

| | | | 1.0% 6-Hydroxyethoxy-2-benzothiazolesulfonamide Gel (Six Days Later) | | | | | |
|---|---|---|---|---|---|---|---|---|
| | | | | IOP (mmHg) | | | | |
| MONKEY # | EYE | TREATMENT | TIME (HR) | IOP | TIME (HR) | IOP | TIME (HR) | IOP |
| 53 | OD | DRUG | 0 | 51 | 3 | 38 | 7 | 36 |
| 48 | OD | DRUG | 0 | 52 | 3 | 50 | 7 | 48 |
| 49 | OD | DRUG | 0 | 34 | 3 | 29 | 7 | 28 |
| 62 | OD | DRUG | 0 | 38 | 3 | 35 | 7 | 37 |
| 60 | OD | DRUG | 0 | 28 | 3 | 27 | 7 | 24 |
| 186 | OD | DRUG | 0 | 30 | 3 | 26 | 7 | 32 |
| MEAN | | | | 38.8 | | 34.2 | | 34.2 |
| S.E. | | | | 4.2 | | 3.7 | | 3.4 |
| MEAN % CHANGE | | | | | | −11.5 | | −10.8 |
| S.E. | | | | | | 3.4 | | 5.1 |
| 56 | OD | CONTROL | 0 | 46 | 3 | 36 | 7 | 46 |
| 47 | OD | CONTROL | 0 | 30 | 3 | 38 | 7 | 33 |
| 55 | OD | CONTROL | 0 | 28 | 3 | 25 | 7 | 27 |
| 63 | OD | CONTROL | 0 | 38 | 3 | 36 | 7 | 34 |
| 52 | OD | CONTROL | 0 | 47 | 3 | 48 | 7 | 52 |
| 187 | OD | CONTROL | 0 | 43 | 3 | 39 | 7 | 32 |
| MEAN | | | | 38.7 | | 37.0 | | 37.3 |
| S.E. | | | | 3.3 | | 3.0 | | 3.9 |
| MEAN % CHANGE | | | | | | −3.0 | | −3.2 |
| S.E. | | | | | | 6.7 | | 5.6 |
| 53 | OS | DRUG | 0 | 30 | 3 | 29 | 7 | 27 |
| 48 | OS | DRUG | 0 | 22 | 3 | 23 | 7 | 23 |
| 49 | OS | DRUG | 0 | 22 | 3 | 26 | 7 | 28 |
| 62 | OS | DRUG | 0 | 25 | 3 | 23 | 7 | 27 |
| 60 | OS | DRUG | 0 | 27 | 3 | 27 | 7 | 24 |
| 186 | OS | DRUG | 0 | 24 | 3 | 24 | 7 | 27 |
| MEAN | | | | 25.0 | | 25.3 | | 26.0 |
| S.E. | | | | 1.3 | | 1.0 | | 0.8 |
| MEAN % CHANGE | | | | | | +1.9 | | +5.2 |
| S.E. | | | | | | 3.7 | | 5.9 |
| 56 | OS | CONTROL | 0 | 33 | 3 | 36 | 7 | 34 |
| 47 | OS | CONTROL | 0 | 19 | 3 | 20 | 7 | 19 |
| 55 | OS | CONTROL | 0 | 23 | 3 | 24 | 7 | 22 |
| 63 | OS | CONTROL | 0 | 22 | 3 | 23 | 7 | 27 |
| 52 | OS | CONTROL | 0 | 19 | 3 | 21 | 7 | 22 |
| 187 | OS | CONTROL | 0 | 32 | 3 | 33 | 7 | 35 |
| MEAN | | | | 24.7 | | 26.2 | | 26.5 |
| S.E. | | | | 2.6 | | 2.7 | | 2.7 |
| MEAN % CHANGE | | | | | | +6.2 | | +7.8 |
| S.E. | | | | | | 1.2 | | 4.2 |

\*\*NOTE:
Percent change values are calculated from individual animal data and may not reflect changes of mean IOP.

TABLE 3

3.0% 6-Hydroxyethoxy-2-benzothiazolesulfonamide Gel

| MONKEY # | EYE | TREATMENT | TIME (HR) | IOP | TIME (HR) | IOP | TIME (HR) | IOP | TIME (HR) | IOP |
|---|---|---|---|---|---|---|---|---|---|---|
| 182 | OD | DRUG | 0 | 50 | 1 | 45 | 3 | 41 | 7 | 37 |
| 189 | OD | DRUG | 0 | 35 | 1 | 33 | 3 | 20 | 7 | 23 |
| 194 | OD | DRUG | 0 | 33 | 1 | 30 | 3 | 30 | 7 | 25 |
| 207 | OD | DRUG | 0 | 55 | 1 | 52 | 3 | 57 | 7 | 55 |
| 50 | OD | DRUG | 0 | 40 | 1 | 35 | 3 | 32 | 7 | 33 |
| 212 | OD | DRUG | 0 | 44 | 1 | 50 | 3 | 45 | 7 | 40 |
| MEAN | | | | 42.8 | | 40.8 | | 37.5 | | 35.5 |
| S.E. | | | | 3.5 | | 3.8 | | 5.3 | | 4.7 |
| MEAN % CONTROL | | | | | | −4.9 | | −14.0 | | −18.5 |
| S.E. | | | | | | 3.8 | | 7.0 | | 5.1 |
| 61 | OD | CONTROL | 0 | 62 | 1 | 62 | 3 | 65 | 7 | 60 |
| 191 | OD | CHANGE | 0 | 52 | 1 | 59 | 3 | 55 | 7 | 62 |
| 206 | OD | CONTROL | 0 | 55 | 1 | 53 | 3 | 59 | 7 | 48 |
| 177 | OD | CONTROL | 0 | 60 | 1 | 57 | 3 | 50 | 7 | 65 |
| 199 | OD | CONTROL | 0 | 55 | 1 | 55 | 3 | 52 | 7 | 50 |
| 192 | OD | CONTROL | 0 | 50 | 1 | 55 | 3 | 42 | 7 | 40 |
| MEAN | | | | 55.7 | | 56.8 | | 53.8 | | 54.2 |
| S.E. | | | | 1.9 | | 1.3 | | 3.2 | | 4.0 |
| MEAN % CHANGE | | | | | | +2.5 | | −3.4 | | −2.9 |
| S.E. | | | | | | 3.1 | | 4.5 | | 5.9 |
| 187 | OS | DRUG | 0 | 27 | 1 | 25 | 3 | 23 | 7 | 23 |
| 189 | OS | DRUG | 0 | 24 | 1 | 29 | 3 | 27 | 7 | 25 |
| 194 | OS | DRUG | 0 | 22 | 1 | 24 | 3 | 23 | 7 | 20 |
| 207 | OS | DRUG | 0 | 26 | 1 | 30 | 3 | 28 | 7 | 29 |
| 50 | OS | DRUG | 0 | 30 | 1 | 24 | 3 | 25 | 7 | 29 |
| 212 | OS | DRUG | 0 | 24 | 1 | 24 | 3 | 25 | 7 | 26 |
| MEAN | | | | 25.5 | | 26.0 | | 25.2 | | 25.3 |
| S.E. | | | | 1.1 | | 1.1 | | 0.8 | | 1.4 |
| MEAN % CHANGE | | | | | | +1.7 | | −0.4 | | −0.6 |
| S.E. | | | | | | 3.1 | | 5.0 | | 4.2 |
| 61 | OS | CONTROL | 0 | 20 | 1 | 20 | 3 | 21 | 7 | 25 |
| 191 | OS | CONTROL | 0 | 29 | 1 | 27 | 3 | 25 | 7 | 27 |
| 206 | OS | CONTROL | 0 | 26 | 1 | 26 | 3 | 25 | 7 | 28 |
| 177 | OS | CONTROL | 0 | 25 | 1 | 16 | 3 | 20 | 7 | 23 |
| 199 | OS | CONTROL | 0 | 23 | 1 | 26 | 3 | 27 | 7 | 25 |
| 192 | OS | CONTROL | 0 | 28 | 1 | 26 | 3 | 27 | 7 | 23 |
| MEAN | | | | 25.2 | | 23.5 | | 24.2 | | 25.2 |
| S.E. | | | | 1.4 | | 1.8 | | 1.2 | | 0.8 |
| MEAN % CHANGE | | | | | | −6.2 | | −3.2 | | +1.4 |
| S.E. | | | | | | 6.7 | | 5.4 | | 6.3 |

**NOTE:
Percent change values are claculated from individual animal data and may not reflect changes of mean IOP.

TABLE 4

3.0% 6-Hydroxyethoxy-2-benzothiazolesulfomaide Gel

| MONKEY # | EYE | TREATMENT | TIME (HR) | IOP | TIME (HR) | IOP | TIME (HR) | IOP | TIME (HR) | IOP |
|---|---|---|---|---|---|---|---|---|---|---|
| 48 | OD | CONTROL | 0 | 49 | 1 | 47 | 3 | 43 | 7 | 44 |
| 180 | OD | CONTROL | 0 | 39 | 1 | 38 | 3 | 38 | 7 | 40 |
| 198 | OD | CONTROL | 0 | 34 | 1 | 35 | 3 | 35 | 7 | 41 |
| 206 | OD | CONTROL | 0 | 52 | 1 | 50 | 3 | 43 | 7 | 57 |
| 53 | OD | CONTROL | 0 | 50 | 1 | 55 | 3 | 52 | 7 | 57 |
| 210 | OD | CONTROL | 0 | 53 | 1 | 45 | 3 | 48 | 7 | 45 |
| MEAN | | | | 46.2 | | 45.0 | | 43.2 | | 47.3 |
| S.E. | | | | 3.2 | | 3.0 | | 2.5 | | 3.1 |
| MEAN % CHANGE | | | | 0.0 | | −2.1 | | −5.8 | | +3.6 |
| S.E. | | | | 0.0 | | 3.4 | | 3.5 | | 5.7 |
| 190 | OD | DRUG | 0 | 38 | 1 | 37 | 3 | 33 | 7 | 35 |
| 177 | OD | DRUG | 0 | 55 | 1 | 50 | 3 | 47 | 7 | 55 |
| 194 | OD | DRUG | 0 | 37 | 1 | 32 | 3 | 29 | 7 | 35 |
| 202 | OD | DRUG | 0 | 42 | 1 | 30 | 3 | 21 | 7 | 28 |
| 203 | OD | DRUG | 0 | 50 | 1 | 53 | 3 | 45 | 7 | 38 |
| 205 | OD | DRUG | 0 | 46 | 1 | 40 | 3 | 55 | 7 | 32 |
| MEAN | | | | 44.7 | | 40.3 | | 38.3 | | 37.2 |
| S.E. | | | | 2.9 | | 3.8 | | 5.2 | | 3.8 |
| MEAN % CHANGE | | | | 0.0 | | −10.1 | | −15.0 | | −16.8 |
| S.E. | | | | 0.0 | | 4.8 | | 9.1 | | 5.8 |
| 48 | OS | CONTROL | 0 | 21 | 1 | 23 | 3 | 22 | 7 | 30 |
| 180 | OS | CONTROL | 0 | 29 | 1 | 27 | 3 | 27 | 7 | 25 |
| 198 | OS | CONTROL | 0 | 27 | 1 | 26 | 3 | 28 | 7 | 28 |
| 206 | OS | CONTROL | 0 | 23 | 1 | 28 | 3 | 26 | 7 | 27 |
| 53 | OS | CONTROL | 0 | 35 | 1 | 30 | 3 | 29 | 7 | 28 |
| 210 | OS | CONTROL | 0 | 25 | 1 | 25 | 3 | 25 | 7 | 25 |
| MEAN | | | | 26.7 | | 26.5 | | 26.2 | | 27.2 |

TABLE 4-continued

| | | | \multicolumn{8}{c|}{3.0% 6-Hydroxyethoxy-2-benzothiazolesulfomaide Gel} |
| | | | \multicolumn{8}{c|}{IOP (mmHg)} |
| MONKEY # | EYE | TREATMENT | TIME (HR) | IOP | TIME (HR) | IOP | TIME (HR) | IOP | TIME (HR) | IOP |
|---|---|---|---|---|---|---|---|---|---|---|
| S.E. | | | | 2.0 | | 1.0 | | 1.0 | | 0.8 |
| MEAN % CHANGE | | | | 0.0 | | +1.1 | | −0.4 | | +5.0 |
| S.E. | | | | 0.0 | | 5.2 | | 4.3 | | 9.3 |
| 190 | OS | DRUG | 0 | 24 | 1 | 25 | 3 | 27 | 7 | 28 |
| 177 | OS | DRUG | 0 | 20 | 1 | 16 | 3 | 18 | 7 | 20 |
| 194 | OS | DRUG | 0 | 18 | 1 | 23 | 3 | 20 | 7 | 23 |
| 202 | OS | DRUG | 0 | 30 | 1 | 28 | 3 | 25 | 7 | 28 |
| 203 | OS | DRUG | 0 | 21 | 1 | 24 | 3 | 21 | 7 | 20 |
| 205 | OS | DRUG | 0 | 27 | 1 | 27 | 3 | 25 | 7 | 27 |
| MEAN | | | | 23.3 | | 23.8 | | 22.7 | | 24.3 |
| S.E. | | | | 1.9 | | 1.7 | | 1.4 | | 1.6 |
| MEAN % CHANGE | | | | 0.0 | | 3.3 | | −1.8 | | 5.5 |
| S.E. | | | | 0.0 | | 6.8 | | 4.8 | | 5.6 |

**NOTE:
Percent change values are calculated from individual animal data and may not reflect changes of mean IOP.

From an examination of the data presented in this example, as well as Tables 1–4, it can be seen that 6-hydroxyethoxy-2-benzothiazolesulfonamide is an effective treating composition for topical treatment of glaucoma in mammalian species such as rabbits and in subhuman primates such as cynomologous monkeys.

What is claimed is:

1. 6-Hydroxyethoxy-2-benzothiazolesulfonamide.

2. A topical composition for eye drop treatment of glaucoma comprising a small but intraocular pressure lowering effective amount of 6-hydroxyethoxy-2-benzothiazolesulfonamide, carbonic anhydrase inhibitor of the formula:

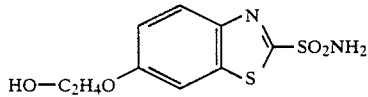

or an ophthalmologically acceptable salt thereof; and an inert, non-eye irritating, non-toxic eye drop diluent.

3. The composition of claim 2 wherein said sulfonamide is at a concentration of from about 0.25% to about 5% by weight of said eye drop treating composition.

4. The composition of claim 2 wherein said sulfonamide is about 0.5% to about 3.0% by weight of said eye drop treating composition.

5. The composition of claim 3 wherein said sulfonamide is about 1% by weight of said eye drop treating composition.

6. The composition of claim 1 wherein said diluent is an isotonic eye treatment carrier, diluent formulation buffered to a pH of from about 4.0 to about 8.0, and containing small but effective amounts of a wetting agent and an anti-bacterial agent.

7. The composition of claim 2 wherein said diluent is an isotonic eye treatment carrier, diluent formulation buffered to a pH of from about 6.8 to about 7.8, and containing small but effective amounts of a wetting agent and an anti-bacterial agent.

8. The composition of claim 5 wherein said wetting agent is a wetting agent of pharmaceutical acceptability.

9. The composition of claim 7 wherein said wetting agent is Tween 80.

10. The composition of claim 6 wherein said anti-bacterial agent is benzalkonium chloride.

11. The composition of claim 9 wherein the amount of said anti-bacterial is from .004% to .02% by weight of said eye drop treatment composition.

12. The composition of claim 2 wherein said diluent is a gel.

13. A method of topically treating glaucoma with eye drops to reduce intraocular eye pressure, said method comprising: topically applying to the eye a small, but intraocular pressure lowering effective amount of 6-hydroxyethoxy-2-benzothiazolesulfonamide or an ophthalmologically acceptable salt thereof, in combination with an inert, non-irritating non-toxic eye drop diluent.

14. The method of claim 13 wherein said 6-hydroxyethoxy-2-benzothiazolesulfonamide is present at a concentration of from about 0.25% to about 5.0% by weight of said compound and diluent combination.

* * * * *